(12) United States Patent
Lezdey et al.

(10) Patent No.: US 6,468,557 B1
(45) Date of Patent: Oct. 22, 2002

(54) METHOD FOR TREATING INFECTIOUS VIRAL DISEASES

(75) Inventors: John Lezdey, Indian Rocks Beach; K. Anne Kronis, Tampa; Darren Lezdey, Indian Rocks Beach, all of FL (US)

(73) Assignee: AlphaMed Pharmaceutical Corp., Clearwater, FL (US)

( * ) Notice: Subject to any disclaimer, the term of this patent is extended or adjusted under 35 U.S.C. 154(b) by 0 days.

(21) Appl. No.: 09/756,616

(22) Filed: Jan. 5, 2001

(51) Int. Cl.⁷ .......................... A61K 9/127; A61K 9/00; A61K 9/70; A61F 13/00; A01N 25/00
(52) U.S. Cl. .................. 424/450; 424/400; 424/443; 424/449; 514/937; 514/944
(58) Field of Search .................. 424/400, 443, 424/449, 450; 514/937, 944

(56) References Cited

U.S. PATENT DOCUMENTS

| | | | | | |
|---|---|---|---|---|---|
| 4,906,476 | A | * | 3/1990 | Radhakrishnan | 424/450 |
| 5,192,802 | A | * | 3/1993 | Rencher | 514/535 |
| 5,637,616 | A | * | 6/1997 | Sharpe et al. | 514/562 |
| 5,843,979 | A | * | 12/1998 | Wille et al. | 514/408 |

* cited by examiner

*Primary Examiner*—Thurman K. Page
*Assistant Examiner*—Humera N. Sheikh

(57) ABSTRACT

The present invention provides for the treatment of an individual suffering from infections from herpes virus or human papilloma virus by utilizing a cromolyn compound. The treatment includes the use of a corticosteroid or L-lysine that can be administered separately or in combination.

7 Claims, No Drawings

METHOD FOR TREATING INFECTIOUS VIRAL DISEASES

FIELD OF THE INVENTION

The present invention relates to the treatment of infectious viral diseases. More particularly, there is provided the treatment of viral infections caused by herpes simplex virus (HSV) or human papilloma virus (HPV) with a cromolyn compound.

BACKGROUND OF THE INVENTION

There are two immunologic types of herpes simplex virus (HSV), HSV-1 and HSV-2. HSV-1 commonly causes herpes labialis and keratitis. HSV-2, usually genital, is transmitted primarily by direct contact with lesions, most often venereally, and also produces skin lesions.

Shingles is believed to be a result of HSV infection.

Human papilloma virus (HPV) has been implicated in vulvovaginities, genital warts and cervical carcinoma.

Treatment in most cases is the use of topical steroids, antibiotics, radiation or surgical excision. None of the treatments are particularly effective since the virus, such as in the case of HSV, can remain dormant in nerve ganglia and can be triggered by immunosuppression, stress, illness and the like. In sexually transmitted diseases (STD) there can be other viruses or bacteria present which also requires treatment.

When lesions occur they can be painful and highly infectious. Painkillers such as lidocaine, DMSO and the like which can be used by such treatment does not reduce the lesions or other skin eruptions or reduce the degree of infectivity of the disease. The protease inhibitors, which are generally useful for HIV infections, have not been effective in controlling the disease. Treatment has been limited to reducing pain or preventing further skin eruptions.

In HSV diseases it has been found that there is a release in serine proteases as well as tumor necrosis factor-alpha (TNF-$\alpha$) as a result of mast cell degranulation. These medicators are involved in the formation of lesions and other skin eruptions, which remain infectious.

In vulvovaginitis and cervical carcinoma there is an increase of TNF-$\alpha$.

Warts, herpes warts and HPV warts all release serine proteases and are involved in inflammatory processes involving mast cells.

U.S. Pat. No. 5,492,889 to Lezdey et al, which is herein incorporated by reference, discloses the treatment of mast cell tumors by the administration of alpha 1-antitrypsin alone or in combination with other serine protease inhibitors.

SUMMARY OF THE INVENTION

The present invention provides a method of treating infectious viral diseases, which commonly result in skin eruptions. More particularly, there is provided the treatment of disease caused by herpes simplex virus (HSV) and human papilloma virus (HPV) by the use of a cromolyn compound.

According to one embodiment of the invention, there is provided the treatment of HSV-1, HSV-2, HPV and the skin eruptions caused thereby through the use of a cromolyn compound. More specifically, the treatment provides either topically or systemically administrating a composition containing an effective amount of a cromolyn compound which includes cromolyn, cromolyn sodium, disodium cromolyn, the lower alkyl esters thereof and other alkali metal salts.

Although a cromolyn compound can be used to relieve the pain and itching caused by the skin eruptions, the use of lidocaine and DMSO expedites elimination of the irritation.

Advantageously, L-lysine can be topically administered with the cromolyn compound and/or taken orally separately.

According to another embodiment of the invention there is provided the treatment of individuals having infectious lesions resulting from HSV-1, HSV-2 or HPV by treatment with a cromolyn compound which prevent the degranulation of mast cells, control the levels of tryptase, control the release of histamines, and prevent or control the release of TNF-$\alpha$. The treatment includes providing a composition for topical administration preferably with a penetrating agent or by formation of an occlusive bandage such as with a vasoline type carrier, especially AQUAPHOR, or penetrating liposomes or DMSO.

It is a general object of the invention to provide a composition and method for treating infections and skin eruptions caused by HSV-1, HSV-2 and HPV.

It is a further object of the invention to provide a composition for treating individuals having virally induced warts, especially genital warts.

It is another object of the invention to treat HPV induced carcinoma by controlling TNF-$\alpha$ to retard cellular proliferation.

It is yet another object of the invention to treat oozing viral lesions which contain the serine proteases to reduce infections.

DESCRIPTION OF THE PREFERRED EMBODIMENTS

In accordance with one embodiment of the invention, there is provided a method for the treatment of individuals suffering from infections from HSV-1, HSV-2, HPV or symptoms thereof by the administration of a composition comprising a cromolyn compound which can bind with the serine proteases and prevent mast cell degranulation. The method consists of the administration of an effective therapeutic amount of a cromolyn compound selected from the group consisting of cromolyn, cromolyn sodium, disodium cromolyn, the alkali salts thereof, the lower alkyl esters or derivatives thereof.

Accordingly, a composition containing at least about 0.5 to 5% by weight of the cromolyn compound in a suitable pharmaceutical vehicle is topically administered to the site of the skin lesion or eruption and/or injected or infused depending upon the disease.

A corticosteroid may be included in the topical composition. The treatment provides immediate relief of pain since the kinins and kallikreins can be controlled. The patient can be treated daily until the lesions or skin eruptions disappear.

A cocktail of a cromolyn compound with other treating antiviral compounds is particularly effective because there is provided a broader spectrum of treatment since other types of wart viruses may be involved or other infections present. Because other infections may be present, the spectrum of anti-viral activity can be increased by including about 0.5 to 5% by weight of L-lysine, a low cost amino acid.

Cromolyn compounds have been found to play a major role in the direct inactivation of the mediators of inflammation involved in viral infections. The almost immediate disappearance of pain indicates that there can be a control of the kinins as well. A cocktail of cromolyn compounds, their salts or derivatives, appears to provide the quickest healing when used in combination with L-lysine or a corticosteroid for topical application. L-lysine may be administered separately and orally if desired when infections are present.

According to another embodiment of the invention, there is provided a method for treating cervical carcinoma resulting from HPV by preventing further infection and preventing cellular proliferation by controlling TNF-α. If the disease is discovered early, the abnormal proliferation occurs in the lower one-third of the epithelium so that the cromolyn compounds can be effective when used in combination with a penetrating agent.

The drug can be administered in unit dosage form containing about 10 to 20 mg per day depending on the severity of the disease. The use of controlled release substances, for example, liposomes, diketopyperazine microparticles as disclosed by U.S. Pat. Nos. 5,620,708 and 5,503,852 which are herein incorporated by reference, and the delivery systems of U.S. Pat. No. 5,620,708 which is herein incorporated by reference. Most preferable, is a salve comprising an occlusive bandage forming composition such as vasoline or AQUAPHOR containing at least about 0.5 to 5% by weight of the cromolyn compound and optionally L-lysine and/or a corticosteroid.

Arginine containing compounds have been found to assist in transdermal delivery of drugs. About 0.25 to 1% by weight of L-arginine will help in the delivery of the drug through the skin.

The corticosteroids which can be used in the treatment of the diseases include triamcinolone acetonide, fluroandrenolide, prednisone, beclomethasone valerate, amcinolone, dexamethasone, betamethasone valerate, halocinonide, clocortolone and hydrocortisone valerate or the like.

The following examples further illustrate the practice of this invention, but are not intended to be limiting thereof. It will be appreciated that the selection of actual amounts of specific cromolyn compounds to be administered to any individual patient will fall within the discretion of the attending physician and will depend on the patient's age, weight, sex, stage of disease and like factors uniquely within the purview of the attending physician.

Example 1

A topical composition for the treatment of patients having genital warts, HPV eruptions or shingles by admixing the following:

| Ingredients | Amount |
| --- | --- |
| AQUAPHOR | 200 mg |
| Cromolyn sodium | 10 mg |
| triamcinolone acetonide | 0.5 mg |
| water | 1 ml |

Optionally, about 10 mg of L-lysine can be included. Daily use for about one week is sufficient to eliminate the eruptions.

Example 2

A gel is prepared for treating warts, shingles or lesions by admixing the following ingredients:

| | Ingredient | Wt % |
| --- | --- | --- |
| 1. | Propylene Glycol | 43.44 |
| 2. | Carbopol | 2.10 |
| 3. | Dipropylene glycol | 10.00 |
| 4. | Xanthan gum | 0.15 |
| 5. | Ethoxydiglycol | 15.00 |
| 6. | Dimethylisosorbide | 10.00 |
| 7. | Ascorbic Acid | 2.00 |
| 8. | Chloroxylenol | 0.20 |
| 9. | Linoleamidopropyl PG-diammonium chloride phosphate | 1.50 |
| 10. | Glycereth 4.5 Lactate | 2.00 |
| 11. | Aloe Vera Gel | 2.00 |
| 12. | Cromolyn sodium | 2.00 |
| 13. | Benzalkonium chloride | 0.50 |
| 14. | Lysine | 8.00 |
| 15. | Cocamidopropyl PG-ammonium chloride phosphate | 1.00 |

Ingredients 1 and 2 are mixed to disperse and form a gel. About 80% of ingredient 3 is mixed with ingredient 4, added to the gel and slightly heated with the admixture. The balance of 3 is mixed with ingredients 5–10 and added to the gel. Ingredients 11–15 are then admixed and added to the gel at 38 degrees C. After mixing, the pH is adjusted to about 4 and then the gel is brought to room temperature. If desired, suitable buffering agents may be added to achieve a pH <5 for use in the vaginal area.

If desired about 1–2% by weight of vitamin C (ascorbic acid) may be added as an antioxidant and/or about 0.25–1% of L-arginine.

Example 3

A topical lotion for the treatment of patients with warts, shingles or lesions is prepared by admixing the following ingredients:

| Ingredient | Wt % |
| --- | --- |
| Propylene Glycol Stearate | 9.50 |
| Isocetyl alcohol | 5.00 |
| PEG-100 Stearate | 1.20 |
| Cromolyn disodium | 2.00 |
| Methyl paraben | 0.20 |
| Propylene glycol | 13.10 |
| Sorbitan palmitate | 0.60 |
| L-Lysine | 6.00 |
| Water | q.s. |
| | 100 |

Example 4

A pilot study was performed in the treatment of herpes simplex eruptions and human papilloma virus warts utilizing the composition of Example 2.

Three patients with HSV-1 eruptions about their mouth after three days of treatment had a disappearance of lesions or eruptions.

One patient with HPV warts after a twice daily application of the composition resulted in disappearance of the warts in one week.

What is claimed is:
1. A method for treating viral infections and skin eruptions caused by herpes virus or human papilloma virus which comprises administering a therapeutically effective amount of a composition containing a cromolyn compound selected from the group consisting of cromolyn, cromolyn sodium, disodium cromolyn the lower alkyl esters, salts and derivatives thereof, in a liposome carrier.

2. The method of claim 1 which comprises further administering a therapeutically effective amount of L-lysine.

3. The method of claim 1 wherein L-lysine is administered separately.

4. The method of claim 1 wherein said composition includes a steroid or a non-steroidal anti-inflammatory agent.

5. The method of claim 1 wherein said composition includes an anti-infective agent.

6. The method of claim 1 wherein said composition contains lidocaine.

7. The method of claim 1 wherein said composition contains an effective amount of L-arginine or an arginine containing compound to assist in penetration into the skin.

* * * * *